(12) United States Patent
Ford et al.

(10) Patent No.: US 11,013,742 B2
(45) Date of Patent: *May 25, 2021

(54) CHOLESTERYL ESTER TRANSFER PROTEIN (CETP) INHIBITOR AND PHARMACEUTICAL COMPOSITIONS COMPRISING SAID INHIBITOR FOR USE IN THE TREATMENT OR PREVENTION OF CARDIOVASCULAR DISEASES

(71) Applicant: DEZIMA PHARMA B.V., Breda (NL)

(72) Inventors: John Ford, Cambridgeshire (GB); Patrick Round, Suffolk (GB); John Kastelein, Amsterdam (NL); Atsuhiro Kawaguchi, Osaka (JP); Koichi Tomiyasu, Osaka (JP); Kozo Oka, Osaka (JP)

(73) Assignee: DEZIMA PHARMA B.V., DC Narden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/844,996

(22) Filed: Apr. 9, 2020

(65) Prior Publication Data

US 2020/0230138 A1 Jul. 23, 2020

Related U.S. Application Data

(62) Division of application No. 15/117,154, filed as application No. PCT/NL2014/050068 on Feb. 5, 2014, now Pat. No. 10,653,692.

(51) Int. Cl.
*A61K 31/506* (2006.01)
*A61K 9/00* (2006.01)

(52) U.S. Cl.
CPC .......... *A61K 31/506* (2013.01); *A61K 9/0053* (2013.01)

(58) Field of Classification Search
CPC .................................................... A61K 31/506
USPC ....................................................... 514/272
See application file for complete search history.

(56) References Cited

U.S. PATENT DOCUMENTS

| 7,872,126 B2 * | 1/2011 | Kubota .................... A61P 9/00 544/298 |
| 10,300,059 B2 * | 5/2019 | Ford .................... A61K 31/505 |

FOREIGN PATENT DOCUMENTS

WO WO-2005/095409 A2 10/2005

OTHER PUBLICATIONS

Marriott, Pharmaceutical Compound and Dispensing, Second Edition, 2010, 1-288.*
Ansel, Pharmaceutical Dosage Forms and Drug Delivery Systems, 1999.*
Barter PJ, Ballantyne CM, Carmena R et al. Apo B versus cholesterol in estimating cardiovascular risk and in guiding therapy: report of the thriy-person/ten-country panel. J Intern Med. 2006;259:247-258.
Barter PJ, Caulfield M, Eriksson M et al. Effects of torcetrapib in patients at high risk for coronary events. N Engl J Med. 2007;357:21009-2122.
Barter PJ, Rye K-A, Beltangady MS et al. Relationship between atorvastatin dose and the harm caused by torcetrapib. J Lipid Res. 2012;53:2436-2442.
Barter PJ, Rye KA. Cholesteryl ester transfer protein inhibition as a strategy to reduce cardiovascular risk. J Lipid Res. 2012;53:1755-1766.
Bloomfield D, Carlson GL, Aditi Sapre BS et al. Efficacy and safety of the cholesteryl ester transfer protein inhibitor anacetrapib as monotherapy and coadministered with atorvastatin in dyslipidemic patients. Am Heart J. 2009;157:352-360.
Bochem AE, Kuivenhoven JA, Stroes ESG. The promise of cholesteryl ester transfer protein (CETP) inhibition in the treatment of cardiovascular disease. Curr Pharm Des. 2013;19:3143-3149.
Cholesterol Treatment Trialists (CTT) Collaboration. Efficacy and safety of more intensive lowering of LDL cholesterol: a meta-analysis of data from 170000 participants in 26 randomised trials. Lancet. 2010;13:1670-1681.
Dansky HM, bloomfield D, Gibbons P et al. Efficacy and safety after cessation of treatment with the cholesteryl ester transfer protein inhibitor anacetrapib (MK-0859) in patients with primary hypercholesterolemia or mixed hyperlipidemia. Am Heart J. 2011;162:708-716.
Florvall G, Basu S, Larsson A. Apolipoprotein A1 is a stronger prognostic marker than HDL and LDL cholesterol for cardiovascular disease and mortality in elderly men. J Gerontol A Biol Sci Med Sci. 2006;61:1262-1266.

(Continued)

*Primary Examiner* — Nizal S Chandrakumar
(74) *Attorney, Agent, or Firm* — Foley & Lardner LLP

(57) ABSTRACT

The present invention relates to a cholesteryl ester transfer protein (CETP) inhibitor:

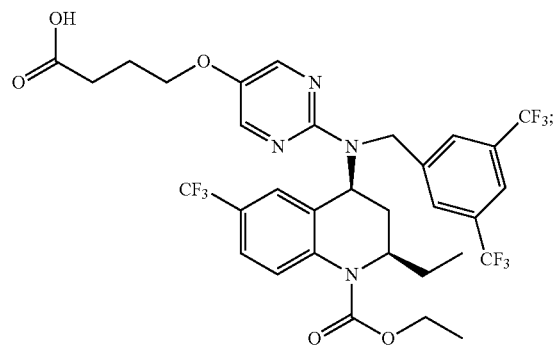

(hereinafter referred to as Compound A) for use in the treatment of subjects suffering from or having an increased risk for cardiovascular diseases, in particular hyperlipidemia or mixed dyslipidemia. A further aspect of the present invention relates to a pharmaceutical composition for use in the treatment of subjects suffering from or having an increased risk for cardiovascular diseases, wherein the composition comprises a therapeutically effective amount of said Compound A CETP inhibitor.

6 Claims, No Drawings

(56) References Cited

OTHER PUBLICATIONS

Forrest MJ, Bloomfield D, Briscoe RJ et al. Torcetrapib-induced blood pressure elevation is independent of CETP inhibition and is accompanied by increasing circulating levels of aldosterone. Br J Pharmacol. 2008;154:1465-1473.

International Search Report and Written Opinion for PCT/NL2014/050068 dated Apr. 4, 2014 (8 pages).

Jaeger BR, Richter Y, Nagel E et al. Longitudinal cohort study on the effectiveness of lipid apheresis treatment to reduce high lipoprotein(a) levels and prevent major adverse coronary events. Nat Clin Pract Cardiovasc Med. 2009;6:229-239.

Johannsen TH, Frikke-Schmidt R, Schou J, Nordestgaard BG, Tybjaerg-Hansen A. Genetic inhibition of CETP, ischemic vascular disease and mortality, and possible adverse effects. J Am Coll Cardio. 2012;60:2041-2048.

Kamstrup PR, Benn M, Tybjaerg-Hansen A, Nordestgaard BG. Extreme lipoprotein(a) levels and risk of myocardial infarction in the general population: The Copenhagen city heart study. Circulation. 2008;117:176-184.

Kamstrup PR, Tybjaerg-Hansen A, Nordestgaard BG. Lipoprotein(a) and risk of myocardial infarction—genetic epidemiologic evidence of causality. Scand J Clin Lab Invest. 2011;71:87-93.

Kastelein JJP, van Leuven SI, Burgess L et al. Effect of torcetrapib on carotid atherosclerosis in familial hypercholesterolemia. N Engl J Med. 2007;356:1620-1630.

Krishna R, Bergman AJ, Fallon et al. Multiple-dose pharmacodynamics and pharmacokinetics of anacetrapib, a potent cholesteryl ester transfer protein (CETP) inhibitor, in healthy subjects. Clin Pharmacol Ther. 2008;84:679-683.

Krishna, Garg A, Panebianco D et al. Single-dose pharmacokinetics and pharmacodynamics of anacetrapib, a potent cholesteryl ester transfer protein (CETP) inhibitor, in healthy subjects. Br J Clin Pharmacol. 2009;68:535-545.

Luscher TF, Taddei S, Kaski JC, et al. Vascular effects and safety of dalcetrapib in patients with or at risk of coronary heart disease: the dal-VESSEL randomized clinical trial. Eur Heart J. 2012;33:857-65.

Nicholls SJ, Brewer HB, Kastelein JJP et al. Effects of the CETP inhibitor evacetrapib administered as monotherapy or in combination with statins on HDL and LDL cholesterol. JAMA. 2011;306:2099-2109.

Nicholls SJ, Tuzcu EM, Brennan DM, Tardif J-C, Nissen SE. Cholesteryl ester transfer protein inhibition, high-density lipoprotein raising, and progression of coronary atherosclerosis. Insights from Illustrate (Investigation of Lipid Level Management Using Coronary Ultrasound to Assess Reduction of Atherosclerosis by CETP Inhibition and HDL Elevation). Circulation. 2008;118:2506-2514.

Nordestgaard BG, Chapman MJ, Ray K et al. Lipoprotein(a) as a cardiovascular risk factor: current status. Eur Heart J. 2010;31:2844-2853.

Okamoto H, Yonemori F, Wakitani K, Minowa T, Maeda K, Shinkai H. A cholesteryl ester transfer protein inhibitor attenuates atherosclerosis in rabbits. Nature. 2000;406:203-207.

Ridker PM, Pare G, Parker AN, Zee RYL, Miletich JP, Chasman DI. Circ Cardiovasc Genet. 2009;2:26-33.

Roger VL, Go AS, Lloyd-Jones DM et al. Heart disease and stroke statistics—2012 Update: A report from the American Heart Association. Circulation. 2012;125:e12-e230.

Schwartz GG, Olsson AG, Abt M et al. Effects of dalcetrapib in patients with recent acute coronary syndrome. N Engl J Med. 2012;367:2089-2099.

Simic B, Hermann M, Shaw SG et al. Torcetrapib impairs endothelial function in hypertension. Eur Heart J. 2012;33:1615-1624.

Stein EA, Stroes ES, Steiner G, et al. Safety and tolerability of dalcetrapib. Am J Cardiol. 2009;104:82-91.

Thanassoulis G, Campbell CY, Owens DS et al. Genetic associations with valvular calcification and aortic stenosis. N Engl J Med. 2013;368:503-512.

The Emerging Risk Factors Collaboration. Lipoprotein(a) concentration and the risk of coronary heart disease, stroke and nonvascular mortality. JAMA. 2009;302:412-423.

The Emerging Risk Factors Collaboration. Major lipids, apolipoproteins, and risk of vascular disease. JAMA. 2009;302:1993-2000.

Thompson A, Di Angelantonio E, Sarwar N, Erqou S, Saleheen D, Dullaart RPF, Keavney B, Ye Z, Danesh J. JAMA. 2008;299:2777-2788.

Vergeer M, Bots ML, van Leuven SI, Basart DC, Sijbrands EJ, Evans GW, Grobbee DE, Visseren FL, Stalenhoef AF, Stroes ES, Kastelein JJP. Cholesteryl ester transfer protein inhibitor torcetrapib and off-target toxicity: pooled analysis of the rating atherosclerotic disease change by imaging with a new CETP inhibitor (RADIANCE) trials. Circulation. 2008;118:2515-2522.

Voight BF, Peloso GM, Orho-Melander M et al. Plasma HDL cholesterol and risk of myocardial infarction: a mendelian randomisation study. Lancet. 2012;380:572-580.

Walldiius G, Jungner I. Rationale for using apolipoprotein B and apolipoproteins A-1 as indicators of cardiac risk and as targets for lipid-lowering therapy. Eur Heart J. 2005;26:210-212.

\* cited by examiner

CHOLESTERYL ESTER TRANSFER PROTEIN (CETP) INHIBITOR AND PHARMACEUTICAL COMPOSITIONS COMPRISING SAID INHIBITOR FOR USE IN THE TREATMENT OR PREVENTION OF CARDIOVASCULAR DISEASES

This application is a continuation of U.S. Non-Provisional application Ser. No. 15/117,154, filed Aug. 5, 2016, which is a National Stage Application under 35 U.S.C. § 371 of International Application No. PCT/NL2014/050068, having an international filing date of Feb. 5, 2014, which is hereby incorporated by reference in its entirety.

TECHNICAL FIELD OF THE INVENTION

The present invention relates to a cholesteryl ester transfer protein (CETP) inhibitor and a pharmaceutical preparation comprising said CETP-inhibitor for use in the treatment of subjects suffering from or having an increased risk for cardiovascular diseases, in particular hyperlipidemia or mixed dyslipidemia.

BACKGROUND OF THE INVENTION

Prospective epidemiological studies have shown a strong association between low density lipoprotein-cholesterol (LDL-C) levels and cardiovascular disease (CVD) risk (1). The subsequent application of statin therapy to decrease these atherogenic LDL-C levels has resulted in a marked reduction of CVD-related morbidity and mortality: every 1 mmol/L decrease in LDL-C results in an estimated 22% reduction of CVD events and a 10% reduction of all-cause mortality (2). Notwithstanding these impressive benefits, a large residual disease burden persists that has a large impact on both individual patients as well as on global healthcare costs (3). Novel therapeutics are required to reduce further this residual CVD risk in patients.

One new approach which reduces LDL-C and elevates HDL-C levels is to inhibit Cholesterol Ester Transfer Protein (CETP). CETP is a plasma protein secreted primarily by liver and adipose tissue. CETP mediates the transfer of cholesteryl esters from HDL to apolipoprotein B (Apo B)-containing particles (mainly LDL and VLDL) in exchange for triglycerides, thereby decreasing the cholesterol content in HDL in favor of that in (V)LDL. Hence, CETP inhibition has been hypothesized to retain cholesteryl esters in HDL-C and decrease the cholesterol content of the atherogenic Apo B fraction.

Despite the evidence supporting the potential of CETP inhibition in reducing cardiovascular morbidity, clinical development of CETP inhibitors has not been straightforward. The first compound to progress to phase 3 clinical trials was torcetrapib which was dosed at 60 mg. Torcetrapib was shown to increase HDL-C by 72% and decrease LDL-C by 25%, but it was subsequently withdrawn from development owing to safety concerns including an unexpected increase in cardiovascular events and death when in combination with atorvastatin, compared with atorvastatin alone (11).

Although the mechanism of those events is not fully understood, there is increasing evidence that they might have been due to off-target effects of torcetrapib such as increased blood pressure, changes in electrolytes (increases in sodium and bicarbonate and decreases in potassium) and increases in aldosterone, consistent with mineralocorticoid activity (11, 12, 13, 14, 15). There is also some evidence from animal studies that torcetrapib increases expression of endothelin-1, which has been postulated to be have contributed to the apparent (non-significant) increase in cancer deaths in the ILLUMINATE trial (16, 17). These observations could be related to the relatively high dose of torcetrapib.

Subsequently, another CETP inhibitor, dalcetrapib, entered phase 2b clinical trials. Dalcetrapib was shown to be a weak inhibitor that increased HDL-C by 30-40% with minimal effects on LDL-C concentrations but did not appear to exhibit the off-target effects of torcetrapib (18, 19, 20). Recently, dalcetrapib development has also been terminated on the grounds of futility in a Phase 3 study where the drug was dosed at 600 mg. Lack of efficacy was probably related to modest CETP inhibition (18).

Two more CETP inhibitors, anacetrapib and evacetrapib, are currently in phase 3 clinical trials. Data from phase 2 studies suggest that both are CETP inhibitors without mineralocorticoid activity. Anacetrapib 200 mg once daily has been shown to increase HDL C by 97% and decrease LDL-C by 36% in fasted healthy subjects (21) and 150 mg once daily anacetrapib has been shown to increase HDL C by 139% and decrease LDL-C by 40% in patients (22). Evacetrapib (500 mg once daily monotherapy in patients) has been shown to increase HDL-C by 129% and decrease LDL-C by 36% (23).

In the ongoing Phase 3 studies, once daily dose of 100 mg anacetratib is being clinically evaluated, whereas for evacetrapib a once daily dose of 130 mg is being evaluated. Such relatively high amounts of active ingredients may lead to several problems.

Due to the fact that a relatively high amount of the above-mentioned CETP-inhibitors has to be administered, the solid oral dosage forms, such as tablets or capsules, will be relatively big. This causes problems with swallowing of such tablets and capsules. Alternatively, one may choose to administer multiple smaller tablets or capsules; however this has a negative influence on patient compliance and costs.

A further disadvantage of the use of the present CETP-inhibitors is that due to the relatively high dosage which has to be used to obtain CETP-inhibition, more and stronger side effects may occur. This can have a negative influence on both the physical well-being of the patient as well as on patient compliance. Moreover, due to a lower bioavailability of the known CETP-inhibitors, inter-subject pharmacokinetic variability may occur. Furthermore, since a relatively high dose is needed for the known CETP-inhibitors (such as anacetrapib) to be effective, it will take several years to eliminate these CETP-inhibitors from the body (reference The American Journal of Cardiology available online 4 Oct. 2013: Evaluation of Lipids, Drug Concentration, and Safety Parameters Following Cessation of Treatment With the Cholesteryl Ester Transfer Protein Inhibitor Anacetrapib in Patients With or at High Risk for Coronary Heart Disease Antonio M. Gotto Jr. et al.).

Hence, a need remains for the provision of a potent and well tolerated CETP-inhibitor and a pharmaceutical composition thereof, which does not show the above mentioned disadvantages.

SUMMARY OF THE INVENTION

A first aspect of the present invention relates to the compound

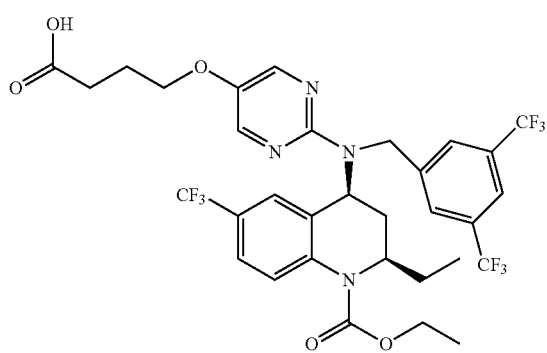 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(hereinafter referred to as Compound A) or a pharmaceutically acceptable salt thereof for use in the treatment of subjects suffering from or having an increased risk for cardiovascular diseases, wherein the dose of Compound A administered to said subjects ranges from 1 to 25 mg per day.

A second aspect of the present invention relates to a pharmaceutical composition for use in the treatment of subjects suffering from or having an increased risk for cardiovascular diseases, wherein the composition comprises a therapeutically effective amount of
Compound A or a pharmaceutically acceptable salt thereof together with a pharmaceutically acceptable excipient. The dose of Compound A to be administered to the subjects with the pharmaceutical composition according to the present invention preferably ranges from about 1 to 25 mg per day.

Clinical studies have shown that Compound A is a potent CETP-inhibitor. Compared to other known CETP-inhibitors, only a relatively low dose of Compound A is needed to reach near complete CETP inhibition. Typically, repeated once daily dosages as low as 2.5 mg of Compound A have proven to be already sufficient to reach near complete CETP-inhibition. These are considerably lower dosages than had to be used for other CETP-inhibitors.

Moreover, clinical studies have also shown that Compound A is well tolerated and that it does not lead to serious side effects. For instance, there were no clinically significant effects observed on blood pressure or heart rate, nor does Compound A appear to have an effect on serum electrolyte or aldosterone concentrations. Clinical studies also showed that Compound A does not suffer from food effects and that at the claimed dose it does not show prolonged residual effects on cessation of dosing.

A third aspect of the present invention relates to a pharmaceutical composition per se, which composition comprises 1 to 25 mg of Compound A or a pharmaceutically acceptable salt thereof and a pharmaceutically acceptable excipient.

A fourth aspect of the present invention relates to a method for preparing such a composition.

Definitions

The term 'pharmaceutical composition' as used herein has its conventional meaning and refers to a composition which is pharmaceutically acceptable.
The term 'pharmaceutically acceptable' as used herein has its conventional meaning and refers to compounds, material, compositions and/or dosage forms, which are, within the scope of sound medical judgment suitable for contact with the tissues of mammals, especially humans, without excessive toxicity, irritation, allergic response and other problem complications commensurate with a reasonable benefit/risk ratio.

The term 'therapeutically effective amount' as used herein has its conventional meaning and refers to an amount or concentration which is effective in producing the desired effect in a mammal, e.g., in reducing, eliminating, treating, preventing or controlling the symptoms of a disease or condition affecting a mammal, in particular human.

The term 'controlling' is intended to refer to all processes wherein there may be a slowing, interrupting, arresting or stopping of the progression of the diseases and conditions affecting the mammal. However, 'controlling' does not necessarily indicate a total elimination of all disease and condition symptoms, and is intended to include prophylactic treatment.

The term 'excipient' as used herein has its conventional meaning and refers to a pharmaceutically acceptable ingredient, which is commonly used in the pharmaceutical technology for preparing a granulate, solid or liquid oral dosage formulation.

The term 'salt' as used herein has its conventional meaning and includes the acid addition and base salts of Compound A.

The term 'increased risk' has its conventional meaning and refers to a situation in a subject, preferably human, where in individuals, either male or female, have an LDL-cholesterol level above 2.6 mmol/l, such that they are exposed at an increased risk of a cardiovascular event, compared to those with lower levels.

The term 'treatment' as used herein has its conventional meaning and refers to curative, palliative and prophylactic treatment.

The term 'cardiovascular disease' has its conventional meaning and includes arteriosclerosis, peripheral vascular disease, hyperlipidemia, mixed dyslipidemia betalipoproteinemia, hypoalphalipoproteinemia, hypercholesteremia, hypertriglyceridemia, familial-hypercholesteremia, angina, ischemia, cardiac ischemia, stroke, myocardial infarction, reperfusion injury, restenosis after angioplasty, hypertension, cerebral infarction and cerebral stroke.

The term 'unit dosage form' has its conventional meaning and refers to a dosage form which has the capacity of being administered to a subject, preferably a human, to be effective, and which can be readily handled and packaged, remaining as a physically and chemically stable unit dose comprising the therapeutic agent, i.e. Compound A.

DETAILED DESCRIPTION OF THE INVENTION

A first aspect of the present invention relates to the compound:

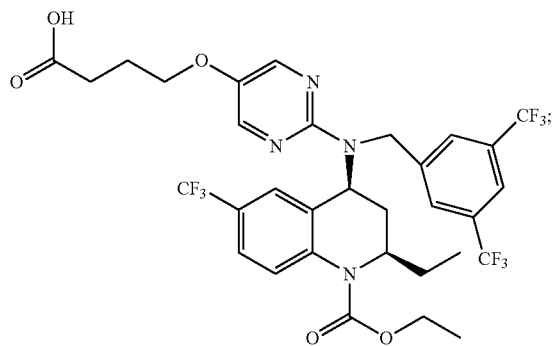 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(hereinafter referred to as Compound A) or a pharmaceutically acceptable salt thereof for use in the treatment of subjects, preferably humans, suffering from or having an increased risk for cardiovascular diseases, wherein the dose of Compound A administered to said subjects ranges from about 1 to 25 mg per day.

Compound A as such has already been described in the European patent application EP1730152, wherein it has been identified as a CETP-inhibitor among many other CETP-inhibitors. Surprisingly, it has now been found that Compound A has exceptionally good pharmacodynamic and pharmacokinetic properties compared to other CETP-inhibitors mentioned in EP 1730152 or used clinically in particular, Compound A has a surprisingly better bioavailability than other known CETP-inhibitors. It has also been found that Compound A may effectively be used clinically in a relatively low dose of about 1 to 25 mg per day, preferably 1 up to and including 10 mg per day. Such doses are preferably administered as a pharmaceutical composition comprising Compound A and an excipient. The prior art does not disclose or suggest that it is possible to use CETP-inhibitors effectively at such a low dose. In this regard reference is made to anacetrapib and evacetrapib, which both required in a clinical setting once daily doses of more than 100 mg.

Preferably, a dose of about 5 to up to and including 10 mg of Compound A per day is used, alternatively a dose of about 5 mg of Compound A, a dose of about 10 mg of Compound A or a dose of about 25 mg of Compound A.

Clinical studies have shown that within the claimed dosage range of about 1 to 25 mg per day it is possible to achieve near complete CETP-inhibition, significant increase of HDL-cholesterol concentration and a remarkable decrease of LDL-cholesterol levels in subjects which have been administered Compound A. The clinical studies have also shown that these effects already occur after a single dose of Compound A.

However, it is preferred to administer to a subject in need of Compound A for extended periods of time the once daily dose of about 1 to 25 mg, preferably a once daily dose of about 5 to 10 mg. Preferably, the subjects in need of Compound A are administered a daily dose of about 1 to 25 mg, preferably about 5 to 10 mg, for 1, 5, 10, 20, 40 52, 100 or 200 weeks.

It is particularly preferred to administer a dose of 1 to 25 mg per day to a subject in need thereof, i.e. a person suffering from cardiovascular diseases or a person having an increased risk for cardiovascular diseases for at least one week, preferably at least three weeks.

Clinical studies have also shown that at a relatively low dose of about 1 to 25 mg of Compound A per day, preferably about 5 to 10 mg per day, no serious adverse effects appeared. For instance, there were no clinically significant effects observed on blood pressure or heart rate, nor does Compound A at the claimed dose appear to have off-target effects, such as on serum electrolyte or aldosterone concentrations. It has also been shown that with the claimed daily dose of Compound A does not suffer from food effects and that at the claimed dose it does not show prolonged residual effects on cessation of dosing due to incomplete drug washout.

The dose of about 1 to 25 mg of Compound A per day, preferably the dose of about 5 to 10 mg, is particularly suitable for use in the treatment of persons suffering from or having an increased risk for cardiovascular diseases, such as arteriosclerosis, peripheral vascular disease, hyperlipidemia, mixed dyslipidemia, hyperbetalipoproteinemia, hypoalphalipoproteinemia, hypercholesteremia, hypertriglyceridemia, familial-hypercholesteremia, angina, ischemia, cardiac ischemia, stroke, myocardial infarction, reperfusion injury, restenosis after angioplasty, hypertension, cerebral infarction, cerebral stroke.

In view of the remarkable decrease of CETP activity, the remarkable decrease of LDL-cholesterol plasma concentration and the significant increase of HDL-cholesterol plasma concentration, the lack of side effects and food effects, it appears that a daily dose of about 1 to 25 mg, preferably 1 to 10 mg of Compound A is particularly suitable for use in the treatment of patients suffering from or having an increased risk for mixed dyslipedimia, hyperlipidemia, or in particular primary hyperlipidemia.

Besides Compound A as such, pharmaceutically acceptable salts thereof may also be used. Pharmaceutically acceptable salts of Compound A include the acid addition and base salts thereof, such as preferably the calcium, potassium or sodium salts. For a review on suitable salts, reference is made "Handbook of Pharmaceutical Salts: Properties, Selection, and Use" by Stahl and Wermuth (Wiley-VCH, Weinheim, Germany, 2002).

A pharmaceutically acceptable salt of Compound A may be readily prepared by mixing together solutions of Compound A and the desired acid or base, as appropriate. The salt may precipitate from solution and be collected by filtration or may be recovered by evaporation of the solvent. The degree of ionisation in the salt may vary from completely ionised to almost non-ionised.

The present invention also relates to pharmaceutically acceptable solvates of Compound A and to pharmaceutical compositions comprising such solvates for use in the treatment of subjects suffering from or having an increased risk for said cardiovascular diseases.

Also within the scope of the invention are so called 'prodrugs' of Compound A. Thus certain derivates of Compound A, which may have little or no pharmacological activity themselves, can when administered into the body be converted into Compound A having the desired CETP-inhibitory activity. Such derivates are within the context of the present invention referred to as 'prodrugs'. Prodrugs in accordance with the invention can, for example, be produced by replacing appropriate functionalities present in Compound A with certain moieties known to those skilled in the art as 'pro-moieties' as described in for example "Design of Prodrugs" by H. Bundgaard (Elsevier, 1985).

The claimed dose of Compound A is preferably administered orally to subjects in need thereof. Preferably, Compound A is administered by means of a pharmaceutical composition. Oral administration may involve swallowing, so that the compound enters the gastrointestinal tract. Alternatively, buccal or sublingual administration may also be employed wherein Compound A enters the blood stream directly from the mouth. Pharmaceutical preparations, as described below, may be developed which facilitate the oral administration.

A second aspect of the present invention relates to a pharmaceutical composition for use in the treatment of subjects suffering from or having an increased risk for cardiovascular diseases, wherein the composition comprises a therapeutically effective amount of Compound A or a pharmaceutically acceptable salt thereof together with a pharmaceutically acceptable excipient. Compound A and its pharmaceutical salts or prodrugs may be as described above.

The dose of Compound A to be administered to the subjects with the pharmaceutical composition according to the present invention preferably ranges from about 1 to 25 mg per day, more preferably from about 5 to 10 mg per day. Alternatively, a dose of about 5 mg of Compound A, a dose of about 10 mg of Compound A or a dose of about 25 mg of Compound A is used.

As already described above, clinical studies have shown that with such a relatively low dose of Compound A, a remarkable decrease of CETP activity, a remarkable decrease of LDL-cholesterol plasma concentration and a significant increase of HDL-cholesterol plasma concentration is reached. Furthermore, it has also been shown that no serious adverse effects occurred at such dose and that no food effects were observed and that Compound A does not show prolonged residual effects on cessation of dosing.

The pharmaceutical composition for use according to the present invention is preferably administered to the subject in need thereof for 1, 5, 10, 20, 40, 52, 100 or 200 weeks. It is particularly preferred to administer the pharmaceutical composition to a subject in need thereof for at least one week, preferably at least three weeks.

In a preferred embodiment of the present invention, the pharmaceutical composition is formulated as a single unit dosage form. The single unit dosage form is preferably a solid oral dosage form, such as a tablet or capsule. Preferably, the single unit dosage form comprises about 1 to 25 mg of Compound A, preferably about 5 to 10 mg of Compound A. It is particularly preferred to use a solid oral dosage form such as tablet or capsule comprising about 1 to 25 mg, preferably about 5 to 10 mg of Compound A.

Solid oral dosage forms which may be used within the context of the present invention include besides tablets and capsules amongst others caplets, lozenges, pills, mini-tablets, pellets, beads and granules packaged in sachets. Liquid oral dosage forms which may be used for the pharmaceutical preparation of the present invention include, but are not limited to drinks, solutions, beverages and emulsions.

The pharmaceutical composition for use in the present invention comprises besides Compound A also an excipient, i.e. a pharmaceutically acceptable ingredient, which is commonly used in the pharmaceutical technology for preparing granulate, solid or liquid oral dosage formulations.

Examples of categories of excipients include, but are not limited to, binders, disintegrants, lubricants, glidants, fillers and diluents. One of ordinary skill in the art may select one or more of the aforementioned excipients with respect to the particular desired properties of the granulate and/or solid oral dosage form by routine experimentation and without any undue burden. The amount of each excipient used may vary within ranges conventional in the art. The following references which are all hereby incorporated by reference disclose techniques and excipients used to formulate oral dosage forms. See "The Handbook of Pharmaceutical Excipients", 4th edition, Rowe et al., Eds., American Pharmaceuticals Association (2003); and "Remington: The Science and Practice of Pharmacy", 20th edition, Gennaro, Ed., Lippincott Williams & Wilkins (2000).

A third aspect of the present invention relates to a pharmaceutical composition per se comprising about 1 to 25 mg of Compound A or a pharmaceutically acceptable salt thereof and a pharmaceutically acceptable carrier. Preferably, the pharmaceutical composition comprises 5 to 10 mg of Compound A or a pharmaceutically acceptable salt thereof.

Compound A and its pharmaceutical acceptable salts and possible prodrugs may be in the forms as described above.

The pharmaceutical composition is preferably formulated as a single unit dosage form as described above. More preferably, the composition is formulated as a liquid oral dosage form or as a solid oral dosage form, most preferably a tablet or capsule.

In a preferred embodiment the pharmaceutical composition comprises a tablet or capsule comprising about 1 to 25 mg, preferably 5 to 10 mg of Compound A or a pharmaceutically acceptable salt thereof.

A fourth aspect of the present invention relates to a method for preparing the above mentioned pharmaceutical compositions. Pharmaceutical compositions of Compound A may be prepared by means commonly known to the person skilled in the art.

The present invention will be illustrated further by means of the following non-limiting examples

EXAMPLES

In the following examples Compound A was studied in an in vitro assay, ex vivo and clinically. For synthesizing Compound A the method described in the international patent application WO2005095409 was used.

Example 1: In Vitro and Ex Vivo

Experimental Method of In Vitro Assay (a) Human Plasma Preparation

Human blood was obtained from healthy male volunteers using 0.1% EDTA as an anticoagulant, and centrifuged at 3,000 rpm for 15 minutes at 4° C. Human plasma was pooled, and then used for the preparation of $^3$H-labeled HDL or stored at −80° C. for CETP assay until use. The $^3$H-labeled HDL was prepared with human plasma as described by Glenn and Melton (*Methods in enzymology*. 263; 339-351, 1996). The specific gravity of plasma was measured by a hydrometer, and the density was adjusted to 1.125 g/mL by adding solid KBr. After centrifugation at 100,000 rpm for 4 hours at 12° C. (rotor: 100.4, Optima TLX, Beckman), d>1.125 g/mL fraction was dialyzed against 4 L of Tris-saline-EDTA buffer (TSE; 50 mmol/L Tris, 150 mmol/L NaCl, 2 mmol/L EDTA, pH 7.4) for 18 hours at 4° C. [1,2-$^3$H(N)]-Cholesterol (37 MBq/mL) was added to the dialyzed plasma fraction at the amount of 2 μCi/mL. The tube was tightly sealed under $N_2$ gas stream and incubated at 37° C. for 18 hours with gently stirring to allow esterification of radio-labeled cholesterol by endogenous LCAT. The incubated plasma fraction was adjusted to d=1.21 g/mL with solid KBr, and centrifuged at 100,000 rpm, 12° C. for 5 hours. $^3$H-labeled HDL fraction was dialyzed against 2 L of TSE at 4° C. for 18 hours. The radioactivity of $^3$H-labeled HDL was counted in a liquid scintillation counter. $^3$H-labeled HDL was stored at 4° C. until use.

(b) CETP Assay

CETP activity was determined as the rate of $^3$H-labeled CE transfer from donor HDL to acceptor VLDL/LDL. Human plasma (94 μL) was pre-incubated with compounds dissolved in DMSO (1 μL) 24 hours at 37° C., and then incubated for 4 hours at 4° C. or 37° C. with 5 μL of $^3$H-labeled HDL. One hundred μL of phosphotungstate/$MgCl_2$ reagent (Wako pure chemical) were added to precipitate apoB-containing lipoproteins. After centrifugation at 3,000 rpm for 10 minutes at room temperature, the radioactivity of the supernatant was counted in a liquid scintillation counter. CETP activity was determined as the difference of the radioactivity between the samples incubated at 37° C. and 4° C. as follows: % inhibition=100−{dpm (DMSO at 4° C.−test compounds at 37° C.)/dpm (DMSO at 4° C.−DMSO at 37° C.)}×100. The concentration achieving 50% inhibition of CETP activity ($IC_{50}$) was estimated.

Experimental Method of Ex Vivo Assay (a) Compound Administration and Collection of Blood Syrian Golden hamsters were used for the experiment after 1-week acclimatization. After an overnight fast, animals were orally given the compound suspension in 0.5% sodium carboxymethylcellulose in a volume of 10 mL/kg. Under deep anesthesia with ether, blood was collected from the abdominal aorta 3 hours after the administration. For preparation of serum, the collected blood was transferred to a plastic tube containing a clot activator, left still for 15 minutes at room temperature and centrifuged. Serum CETP activities were determined immediately.

(b) Determination of Serum CETP Activity Ex Vivo

Ninety-five μL serum were added to 5 μL of 0.1 mM sodium phosphate buffered saline (pH 7.0) containing 1.5 mM 5,5'-dithio-bis(2-nitrobenzoic acid) in two 96-well V-bottom plates. One plate was incubated at 4° C. and the other was incubated at 37° C. After 18 hours of incubation, each sample was mixed with 100 μL of reagent for precipitation of apolipoprotein B-containing lipoproteins (phospho-tungstate/$MgCl_2$ reagent, Wako pure chemical), left still for 10 minutes at room temperature and centrifuged. Total cholesterol (TC) and free cholesterol (FC) in supernatant were measured using commercial kits (Cholesterol E-test wako, and Free Cholesterol E-test wako; Wako pure chemical). Cholesteryl ester (CE) was calculated by subtracting FC from TC. CETP activity was determined by the following formula:

CETP activity=[CETP transfer]*/[CE value in 4° C. incubation sample]*CETP transfer=[CE value in 4° C. incubation sample]−[CE value in 37° C. incubation sample]

(c) Results

| compound example # | Structural elements at indicated positions | | | | in vitro $IC_{50}$ (μM) human plasma (24 h pre-incubation) | ex vivo (% inhibition) 3 mg/kg (CMC) |
|---|---|---|---|---|---|---|
| | R1 | R2 | R3 | R4 | | |
| Compound A | HO-C(=O)-CH2-CH2-CH2-O- | $CF_3$ | $CH_3$ | $CF_3$ | 0.064 | 79.2 |
| 1 | HO-C(=O)-C6H4-CH2-O- (para) | $CF_3$ | $CH_3$ | $CF_3$ | 0.21 | 57.5 |
| 2 | HO-C(=O)-C6H4-CH2-O- (meta) | $CF_3$ | $CH_3$ | $CF_3$ | 0.23 | 38.4 |
| 3 | HO-C(=O)-CH2-NH-C(=O)-CH2-O- | $CF_3$ | $CH_3$ | $CF_3$ | 0.45 | 5.4 |
| 4 | HO-C(=O)-CH2-N(CH3)-C(=O)-CH2-O- | $CF_3$ | $CH_3$ | $CF_3$ | 0.79 | 8.6 |
| 5 | pyrrolidine-N-C(=O)-CH2-O-, 2-COOH | $CF_3$ | $CH_3$ | $CF_3$ | 1.7 | 6.2 |
| 6 | HO-C(=O)-CH2-CH2-CH2-S(=O)(=O)- | $CF_3$ | $CH_3$ | $CF_3$ | 0.22 | 13.9 |

| compound example # | Structural elements at indicated positions | | | | in vitro IC$_{50}$ (μM) human plasma (24 h pre-incubation) | ex vivo (% inhibition) 3 mg/kg (CMC) |
|---|---|---|---|---|---|---|
| | R1 | R2 | R3 | R4 | | |
| 7 | OH (structure shown) | CF$_3$ | (structure shown) | CF$_3$ | 0.11 | 25.4 |

The core structure is:

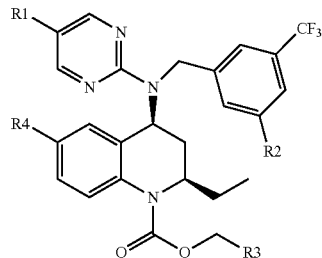

Example 2: Double Blind Randomized Study of Subjects Receiving Multiple Doses of Compound A or Placebo

Study Design

The clinical study was a repeated dose study in 5 groups of Caucasian male subjects aged 18 to 55 years. Each subject received a single oral dose of Compound A/placebo on Day 1, followed by once daily doses on Days 8 to 35 (5 mg Compound A/placebo—Group 1) or Days 8 to 28 (1, 2.5, 10 and 25 mg Compound A/placebo—Groups 2 to 5). All doses were administered at the study center after a standard breakfast. Subjects in each dose group were allocated to study treatment in a ratio of 10 Compound A to 2 placebo. Blood samples for pharmacokinetic and pharmacodynamic (CETP activity, CETP concentration, HDL-C, LDL-C, total cholesterol, triglycerides) assessments were collected from prior to each dose and at intervals throughout the study until 336 hours after the last dose. Secondary pharmacodynamic endpoints (including apolipoproteins A1, A2, B, and E, HDL2-C, HDL3-C, phospholipids, HDL-free cholesterol [HDL-FC], HDL-cholesteryl ester [HDL-CE], HDL-phospholipids [HDL-PL], HDL-triglycerides [HDL-TG], and LDL particle size) were measured at intervals until the last day of dosing. Urine was collected for pharmacokinetics from pre dose and at intervals up to 72 hours after the first and last dose. Safety assessments including adverse events, blood pressure and pulse rate, ECGs, laboratory safety tests (including aldosterone) and physical examinations were conducted throughout both studies.

Analytical Methods

Plasma and urine concentrations of Compound A were determined using validated liquid chromatography with tandem mass spectrometry (LC/MS/MS) methods. The lower limit of quantification (LLQ) for both assays was 0.500 ng/mL. Plasma concentration of CETP was determined using a validated enzyme-linked immunosorbent assay (ELISA) method with a lower limit of quantification (LLQ) of 0.500 μg/mL. CETP activity was determined as the rate of [$^3$H]-labeled CE transfer from donor HDL to acceptor VLDL/LDL. [$^3$H]CE-labeled HDL was added to human plasma and incubated for 4 hours at 37° C. Non-HDL lipoproteins were precipitated and separated from HDL, and the amount of radioactivity in the supernatant was quantitated. CETP activity was determined as the difference of the radioactivity between the samples incubated at 37° C. and 4° C. HDL-C and LDL-C were measured by homogenous enzymatic colorimetric assay using a Modular analyser (Roche Diagnostics). Total cholesterol and triglycerides were measured by homogenous enzymatic assay using a Modular analyser (cholesterol oxidase peroxidase-peroxidase aminophenazone phenol [CHOP-PAP]) method and a glycerol phosphate oxidase [GPO-PAP] method, respectively. ApoA1, ApoA2, ApoB and ApoE were measured by immunoturbidimetry using reagents from Rolf Greiner Biochemica (Germany) and N-apoprotein standard serum from Siemens (Germany). LDL particle size was determined by gradient gel electrophoresis. HDL fraction was separated by a combined ultracentrifugation-precipitation method (Beta-quantification). HDL-2 and HDL-3 fractions were then separated by further ultracentrifugation. Total-cholesterol in HDL, HDL-2 and HLD-3 fractions, free cholesterol in HDL fraction, triglycerides in HDL fraction and phospholipids in plasma and HDL-fraction were measured using enzymatic methods and reagents from Diasys Diagnostics (Germany). The measurements were performed on an Olympus AU600 automatic analyzer and were calibrated using secondary standards from Roche Diagnostics (Total-cholesterol, triglycerides) and Diasys Diagnostics (free cholesterol, phospholipids), respectively. Esterified cholesterol was calculated as the difference between total-cholesterol and free cholesterol.

Statistical Analyses

The sample sizes for the study were chosen based on practical considerations rather than statistical power. The numbers of subjects in each group were considered to be adequate to assess the main objectives of each study. Subjects were allocated to Compound A or placebo in each group by means of a computer-generated randomization code. Pharmacokinetic parameters were determined by non-compartmental methods using WinNonlin software version 4.1 (Pharsight Corporation, USA). All data were listed and summarized by treatment group using descriptive statistics. In the study, maximum percent changes from baseline at each Compound A dose level were compared with pooled placebo using an ANOVA model. All statistical analyses were conducted using SAS version 6.12 or higher (SAS Institute Inc. USA).

Pharmacokinetic Results

In the study, plasma concentrations appeared to increase approximately proportionally to dose following single doses from 1 to 25 mg, although non-proportionality was observed at steady state: 7-fold, 9-fold and 12-fold increases in $C_{min,ss}$, $AUC_{0-tau,ss}$ and $C_{max,ss}$, respectively, for a 25-fold increase in dose. $T_{max}$ was independent of dose with median values of 4 to 6 hours post-dose. Variability was moderate following single and multiple dosing with CVs for $C_{max}$, $C_{min}$ and AUC parameters being ≤33%. Visual inspection of trough concentrations suggests that Compound A approached steady state within 1 to 2 weeks of daily dosing. The mean terminal half-life of Compound A following the last dose was 121 to 151 hours and was independent of dose. A similar half-life was observed between single and multiple dose of 5 to 25 mg of Compound A, respectively. Compound A accumulated with once daily dosing in a dose-dependent manner, with an approximately 6-fold increase at 1 mg through to a 2-fold increase at 25 mg.

Pharmacodynamics Results

Baseline pharmacodynamic parameters were well balanced across treatment groups the study. Compound A strongly inhibited CETP activity in a dose-dependent manner following both single and repeated dosing. Near complete CETP inhibition was observed following repeated doses of 2.5, 5, 10 to 25 mg once daily Compound A (~92 to 99%) (Table 1). This level of inhibition was maintained throughout the repeated dosing period and the maximum effect of each dose was achieved within 1 week of once daily dosing. The duration of inhibition after the last dose was dose-dependent, with activity approaching baseline levels by 2 weeks following the lowest dose (1 mg), but still being approximately 50% below baseline at 2 weeks following 10 and 25 mg dosing. Although CETP activity decreased with Compound A dosing, the concentration of CETP increased in a dose-dependent manner following both single and multiple dosing. CETP concentration increased from baseline by 2.5- to 2.8-fold after 3 weeks of dosing with 10 mg and 25 mg once daily Compound A. CETP concentrations declined in parallel with plasma drug concentrations. Following the cessation of Compound A dosing, such that concentrations were approaching baseline values within 2 weeks following 1 mg and 5 mg Compound A, whereas concentrations were still approximately 1.4-fold higher than baseline at 2 weeks following 10 mg and 25 mg Compound A. The maximum percent changes in CETP activity and CETP concentrations were statistically significantly different from placebo (p<0.0001) at all Compound A dose levels (1 to 25 mg).

HDL-C concentrations increased in a dose-dependent manner following multiple dosing. Once daily Compound A at doses of 2.5 to 25 mg led to marked increases from baseline HDL-C of approximately 96% up to 140%. LDL-C concentrations decreased in a dose-dependent manner with maximum decreases from baseline of approximately 40% to 53% following 2.5 to 25 mg once daily Compound A. The maximum percent changes from baseline were statistically significantly different from placebo (p<0.0001) following once daily Compound A doses of 5 to 25 mg for HDL-C and following 10 and 25 mg for LDL C. HDL-C and LDL-C concentrations started to return towards baseline following cessation of Compound A dosing consistent with the loss of CETP inhibition. There were trends indicating dose-related increases in Apo A-1, Apo E, HDL2-C and HDL3-C, and decreases in Apo B concentrations. Variability was high for all of these variables; nevertheless the data suggest that maximum effects may have been achieved with doses of 5 to 10 mg once daily Compound A. There was no dose-related trend in Apo A2 or phospholipids, but there were dose-related increases in HDL-FC, HDL-CE and HDL-PL and decreases in HDL-TG across the dose range 1 to 10 mg with no further changes noted at 25 mg Compound A. There were no noteworthy changes in LDL particle size. In addition, there was no evidence of any relevant effect of food, age, gender or ethnicity on the pharmacodynamic variables.

Safety

Repeated doses up 25 mg once daily were well tolerated in all subjects. There were no serious adverse events and no subjects withdrew because of adverse events. There were no clinically significant effects on blood pressure or heart rate, ECG variables, physical examination or laboratory safety tests. In particular, Compound A had no effect on serum electrolyte or aldosterone concentrations.

TABLE 1

Maximum percent change from baseline for primary pharmacodynamic variables for Compound A following repeated oral doses in Caucasian male healthy subjects

| Maximum % change from baseline in: Steady State Data | Placebo (Group 1) N = 1 | Placebo (Groups 2-5) N = 8 | Compound A dose (once daily) | | | | |
|---|---|---|---|---|---|---|---|
| | | | 1 mg N = 10 | 2.5 mg N = 10 | 5 mg N = 10 | 10 mg N = 10 | 25 mg N = 10 |
| CETP activity | 21.3 | -8.9 (14.7) | -66.5 (6.4) | -91.6 (6.4) | -90.9 (7.1) | -97.6 (2.9) | -99.4 (1.1) |
| CETP concentration | 34.9 | 19.5 (18.4) | 128 (34.3) | 144 (22.3) | 215 (50.9) | 249 (49.6) | 280 (47.4) |
| HDL-C concentration | -2.7 | 10.7 (20.5) | 37.9 (20.6) | 95.6 (30.4) | 118 (33.2) | 140 (36.4) | 136 (43.9) |
| LDL-C concentration | 25.0 | -8.8 (20.8) | -29.6 (6.9) | -39.1 (14.3) | -41.7 (11.4) | -43.6 (14.6) | -53.2 (15.0) |
| Total cholesterol | 1.4 | -8.1 (18.1) | -12.7 (7.1) | -7.9 (14.2) | -1.4 (12.4) | 3.7 (18.2) | 7.5 (17.2) |

TABLE 1-continued

Maximum percent change from baseline for primary pharmacodynamic variables for Compound A following repeated oral doses in Caucasian male healthy subjects

| Maximum % change from baseline in: Steady State Data | Placebo (Group 1) N = 1 | Placebo (Groups 2-5) N = 8 | Compound A dose (once daily) | | | | |
|---|---|---|---|---|---|---|---|
| | | | 1 mg N = 10 | 2.5 mg N = 10 | 5 mg N = 10 | 10 mg N = 10 | 25 mg N = 10 |
| Triglycerides | −28.8 | −46.1 (20.9) | −50.2 (16.2) | −45.8 (16.5) | −20.3 (20.2) | −22.2 (19.9) | −31.4 (25.8) |

Values are mean (SD)
Group 1 received 5 mg Compound A/placebo on Day 1 and Days 8 to 42.
Groups 2-5 received 1, 2.5, 10 and 25 mg Compound A/placebo on Day 1 and Days 8 to 35.
CHEMICAL NAME AND FORMULA OF COMPOUND A

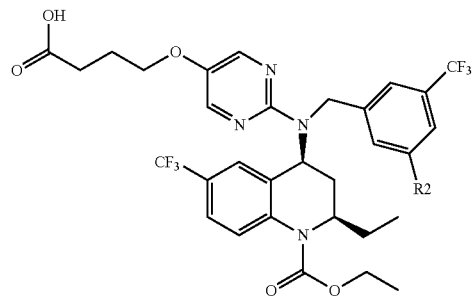

{4-[(2-{[3,5-bis(trifluoromethyl)benzyl][(2R,4S)-1-(ethoxycarbonyl)-2-ethyl-6-(trifluoromethyl)-1,2,3,4-tetrahydroquinolin-4-yl]amino}pyrimidin-5-yl)oxy]butanoic acid}

REFERENCES

1. The Emerging Risk Factors Collaboration. Major lipids, apolipoproteins, and risk of vascular disease. *JAMA.* 2009; 302:1993-2000.
2. Cholesterol Treatment Trialists (CTT) Collaboration. Efficacy and safety of more intensive lowering of LDL cholesterol: a meta-analysis of data from 170000 participants in 26 randomised trials. *Lancet.* 2010; 13:1670-1681.
3. Roger V L, Go A S, Lloyd-Jones D M et al. Heart disease and stroke statistics—2012 Update: A report from the American Heart Association. *Circulation.* 2012; 125:e12-e230.
4. Johannsen T H, Frikke-Schmidt R, Schou J, Nordestgaard B G, Tybjærg-Hansen A. Genetic inhibition of CETP, ischemic vascular disease and mortality, and possible adverse effects. *J Am Coll Cardio.* 2012; 60:2041-2048.
5. Voight B F, Peloso G M, Orho-Melander M et al. Plasma HDL cholesterol and risk of myocardial infarction: a mendelian randomisation study. *Lancet.* 2012; 380:572-580.
6. Thompson A, Di Angelantonio E, Sarwar N, Erqou S, Saleheen D, Dullaart R P F, Keavney B, Ye Z, Danesh J. *JAMA.* 2008; 299:2777-2788.
7. Ridker P M, Pare G, Parker A N, Zee R Y L, Miletich J P, Chasman D I. *Circ Cardiovasc Genet.* 2009; 2:26-33.
8. Okamoto H, Yonemori F, Wakitani K, Minowa T, Maeda K, Shinkai H. A cholesteryl ester transfer protein inhibitor attenuates atherosclerosis in rabbits. *Nature.* 2000; 406:203-207.
9. Barter P J, Rye K A. Cholesteryl ester transfer protein inhibition as a strategy to reduce cardiovascular risk. *J Lipid Res.* 2012; 53:1755-1766.
10. Bochem A E, Kuivenhoven J A, Stroes E S G. The promise of cholesteryl ester transfer protein (CETP) inhibition in the treatment of cardiovascular disease. *Curr Pharm Des.* 2013; 19:3143-3149.
11. Barter P J, Caulfield M, Eriksson M et al. Effects of torcetrapib in patients at high risk for coronary events. *N Engl J Med.* 2007; 357:21009-2122.
12. Kastelein J J P, van Leuven S I, Burgess L et al. Effect of torcetrapib on carotid atherosclerosis in familial hypercholesterolemia. *N Engl J Med.* 2007; 356:1620-1630.
13. Nicholls S J, Tuzcu E M, Brennan D M, Tardif J-C, Nissen S E. Cholesteryl ester transfer protein inhibition, high-density lipoprotein raising, and progression of coronary atherosclerosis. Insights from ILLUSTRATE (Investigation of Lipid Level Management Using Coronary Ultrasound to Assess Reduction of Atherosclerosis by CETP Inhibition and HDL Elevation). *Circulation.* 2008; 18:2506-2514.
14. Vergeer M, Bots M L, van Leuven S I, Basart D C, Sijbrands E J, Evans G W, Grobbee D E, Visseren F L, Stalenhoef A F, Stroes E S, Kastelein J J P. Cholesteryl ester transfer protein inhibitor torcetrapib and off-target toxicity: pooled analysis of the rating atherosclerotic disease change by imaging with a new CETP inhibitor (RADIANCE) trials. *Circulation.* 2008; 118:2515-2522.
15. Forrest M J, Bloomfield D, Briscoe R J et al. Torcetrapib-induced blood pressure elevation is independent of CETP inhibition and is accompanied by increasing circulating levels of aldosterone. *Br J Pharmacol.* 2008; 154:1465-1473.
16. Simic B, Hermann M, Shaw S G et al. Torcetrapib impairs endothelial function in hypertension. *Eur Heart J.* 2012; 33:1615-1624.
17. Barter P J, Rye K-A, Beltangady M S et al. Relationship between atorvastatin dose and the harm caused by torcetrapib. *J Lipid Res.* 2012; 53:2436-2442.
18. Schwartz G G, Olsson A G, Abt M et al. Effects of dalcetrapib in patients with recent acute coronary syndrome. *N Engl J Med.* 2012; 367:2089-2099.

19. Stein E A, Stroes E S, Steiner G, et al. Safety and tolerability of dalcetrapib. *Am J Cardiol.* 2009; 104:82-91.
20. Lüscher T F, Taddei S, Kaski J C, et al. Vascular effects and safety of dalcetrapib in patients with or at risk of coronary heart disease: the dal-VESSEL randomized clinical trial. *Eur Heart J.* 2012; 33:857-65.
21. Krishna R, Bergman A J, Fallon et al. Multiple-dose pharmacodynamics and pharmacokinetics of anacetrapib, a potent cholesteryl ester transfer protein (CETP) inhibitor, in healthy subjects. *Clin Pharmacol Ther.* 2008; 84:679-683.
22. Bloomfield D, Carlson G L, Aditi Sapre B S et al. Efficacy and safety of the cholesteryl ester transfer protein inhibitor anacetrapib as monotherapy and coadministered with atorvastatin in dyslipidemic patients. *Am Heart J.* 2009; 157:352-360.
23. Nicholls S J, Brewer H B, Kastelein J J P et al. Effects of the CETP inhibitor evacetrapib administered as monotherapy or in combination with statins on HDL and LDL cholesterol. *JAMA.* 2011; 306:2099-2109.
24. Dansky H M, Bloomfield D, Gibbons P et al. Efficacy and safety after cessation of treatment with the cholesteryl ester transfer protein inhibitor anacetrapib (MK-0859) in patients with primary hypercholesterolemia or mixed hyperlipidemia. *Am Heart J.* 2011; 162:708-716.
25. Florvall G, Basu S, Larsson A. Apolipoprotein A1 is a stronger prognostic marker than HDL and LDL cholesterol for cardiovascular disease and mortality in elderly men. *J Gerontol A Biol Sci Med Sci.* 2006; 61:1262-1266.
26. Walldius G, Jungner I. Rationale for using apolipoprotein B and apolipoproteins A-1 as indicators of cardiac risk and as targets for lipid-lowering therapy. *Eur Heart J.* 2005; 26:210-212.
27. Barter P J, Ballantyne C M, Carmena R et al. Apo B versus cholesterol in estimating cardiovascular risk and in guiding therapy: report of the thirty-person/ten-country panel. *J. Intern Med.* 2006; 259:247-258.
28. Nordestgaard B G, Chapman M J, Ray K et al. Lipoprotein(a) as a cardiovascular risk factor: current status. *Eur Heart J.* 2010; 31:2844-2853.
29. Kamstrup P R, Tybjaerg-Hansen A, Nordestgaard B G. Lipoprotein(a) and risk of myocardial infarction—genetic epidemiologic evidence of causality. *Scand J Clin Lab Invest.* 2011; 71:87-93.
30. The Emerging Risk Factors Collaboration. Lipoprotein (a) concentration and the risk of coronary heart disease, stroke and nonvascular mortality. *JAMA.* 2009; 302:412-423.
31. Kamstrup P R, Benn M, Tybjaerg-Hansen A, Nordestgaard B G. Extreme lipoprotein(a) levels and risk of myocardial infarction in the general population: The Copenhagen city heart study. *Circulation.* 2008; 117:176-184.
32. Thanassoulis G, Campbell C Y, Owens D S et al. Genetic associations with valvular calcification and aortic stenosis. *N Eng J Med.* 2013; 368:503-512.
33. Jaeger B R, Richter Y, Nagel E et al. Longitudinal cohort study on the effectiveness of lipid apheresis treatment to reduce high lipoprotein(a) levels and prevent major adverse coronary events. *Nat Clin Pract Cardiovasc Med.* 2009; 6:229-239.
34. Krishna, Garg A, Panebianco D et al. Single-dose pharmacokinetics and pharmacodynamics of anacetrapib, a potent cholesteryl ester transfer protein (CETP) inhibitor, in healthy subjects. *Br J Clin Pharmacol.* 2009; 68:535-545.

The invention claimed is:

1. A solid, oral pharmaceutical composition, comprising 5 to 10 mg of compound A:

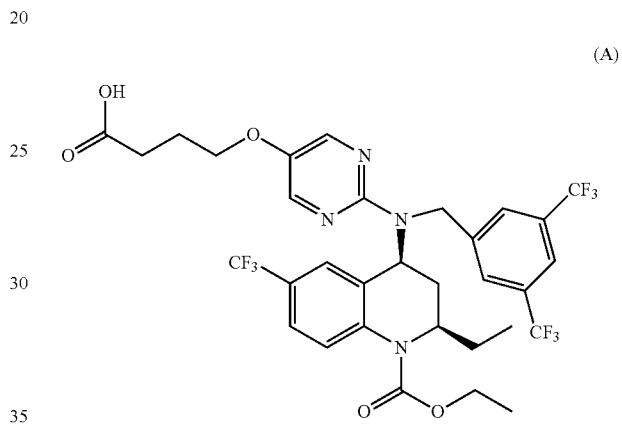

(A)

or a pharmaceutically acceptable salt thereof and a pharmaceutically acceptable excipient, wherein the composition is formulated for once a day administration.

2. The pharmaceutical composition according to claim 1, comprising 5 mg or 10 mg of Compound A.

3. The pharmaceutical composition according to claim 1, wherein the composition is formulated as a tablet or capsule.

4. The pharmaceutical composition according to claim 1, comprising a salt of Compound A, wherein the salt is a calcium, potassium or sodium salt.

5. The pharmaceutical composition according to claim 1, comprising 5 mg of Compound A.

6. The pharmaceutical composition according to claim 1, comprising 10 mg of Compound A.

* * * * *